(12) United States Patent
Miyamoto

(10) Patent No.: US 11,766,240 B2
(45) Date of Patent: Sep. 26, 2023

(54) TRANSRECTAL ULTRASONIC PROBE

(71) Applicant: Hitachi, Ltd., Tokyo (JP)

(72) Inventor: Nobutaka Miyamoto, Tokyo (JP)

(73) Assignee: FUJIFILM Healthcare Corporation, Chiba (JP)

( * ) Notice: Subject to any disclaimer, the term of this patent is extended or adjusted under 35 U.S.C. 154(b) by 127 days.

(21) Appl. No.: 17/191,831

(22) Filed: Mar. 4, 2021

(65) Prior Publication Data
US 2021/0321983 A1  Oct. 21, 2021

(30) Foreign Application Priority Data

Apr. 20, 2020 (JP) .................................. 2020-074581

(51) Int. Cl.
*A61B 8/00* (2006.01)
*A61B 8/12* (2006.01)
*A61B 8/08* (2006.01)

(52) U.S. Cl.
CPC .............. *A61B 8/4444* (2013.01); *A61B 8/12* (2013.01); *A61B 8/445* (2013.01); *A61B 8/4455* (2013.01); *A61B 8/085* (2013.01); *A61B 8/0841* (2013.01)

(58) Field of Classification Search
CPC ......... A61B 8/4444; A61B 8/12; A61B 8/445; A61B 8/4455; A61B 8/0841; A61B 8/085
See application file for complete search history.

(56) References Cited

U.S. PATENT DOCUMENTS 9,259,208 B2    2/2016  Nygaard et al.
2013/0225995 A1*  8/2013  Hashiguchi ............ A61B 1/307
                                                                600/459

FOREIGN PATENT DOCUMENTS

JP          2015-104602 A       6/2015

* cited by examiner

*Primary Examiner* — Christopher Koharski
*Assistant Examiner* — Taylor Deutsch
(74) *Attorney, Agent, or Firm* — MATTINGLY & MALUR, PC

(57) ABSTRACT

A probe, which is a transrectal ultrasonic probe, includes an insertion unit to be inserted into the rectum of a subject. The insertion unit includes a shaft in a slim shape closer to the proximal side, and an insertion tip portion that is connected to the distal end of the shaft and has an acoustic head that transmits and receives ultrasonic waves. The ultrasonic waves are transmitted from the acoustic head laterally to the insertion unit. The extension direction of the shaft from the proximal side toward the distal side is curved in the direction opposite to the direction D in which the acoustic head transmits the ultrasonic waves.

3 Claims, 4 Drawing Sheets

TRANSRECTAL ULTRASONIC PROBE

CROSS REFERENCE TO RELATED APPLICATION

This application claims priority to Japanese Patent Application No. 2020-074581 filed on Apr. 20, 2020, which is incorporated herein by reference in its entirety including the specification, claims, drawings, and abstract.

TECHNICAL FIELD

This description discloses a transrectal ultrasonic probe.

BACKGROUND

An ultrasonic probe transmits and receives ultrasonic waves to and from a subject. The ultrasonic probe is connected to an ultrasonic diagnostic apparatus body (hereinafter referred to as "apparatus body"), transmits ultrasonic waves to the subject according to signals from the apparatus body, and transmits to the apparatus body electric signals responsive to reflected waves from the subject. The apparatus body forms and displays ultrasonic images based on the electric signals from the ultrasonic probe.

There are various types of ultrasonic probes. For example, there is an in-body cavity ultrasonic probe a part of which is inserted into the body cavity of a subject and irradiates the test site with ultrasonic waves from the inside of the body cavity. Examples of in-body cavity ultrasonic probes include transrectal ultrasonic probes that are inserted into the rectum of a subject. Transrectal ultrasound probes are often used in the case where the test site is a prostate.

A transrectal ultrasonic probe having a curved insertion unit to be inserted into a rectum has been conventionally proposed. JP 2015-104602 A, for example, discloses a transrectal ultrasonic probe in which the insertion unit to be inserted into the rectum is curved so that the ultrasonic radiation plane coincides with the section in a CT or MRI image without largely tilting the transrectal ultrasonic probe inserted in the rectum, and the probe includes an ultrasonic oscillator that transmits ultrasonic waves in the direction in which the tip of the curved insertion unit extends. The transrectal ultrasonic probe according to JP 2015-104602 A reduces the burden on the subject when the ultrasonic radiation plane is made to coincide with the section in a CT or MRI image.

A transrectal ultrasonic probe inserted into the rectum of a subject may impose a burden (for example, pain) on the subject. It is therefore desirable to reduce the burden on the subject when the transrectal ultrasonic probe is inserted into the rectum. Reducing the burden on the subject when the transrectal ultrasound probe is inserted into the rectum also facilitates insertion of the transrectal ultrasonic probe into the rectum of the subject, from the perspective of an operator, such as a doctor, who inserts the transrectal ultrasound probe into the rectum of the subject.

It is an advantage of a transrectal ultrasonic probe disclosed in this description to be a transrectal ultrasonic probe that reduces the burden of a subject when inserted into the rectum of the subject. Alternatively, it is an advantage of a transrectal ultrasonic probe disclosed in this description to be a transrectal ultrasonic probe that can more easily be inserted into the rectum of the subject.

SUMMARY

A transrectal ultrasonic probe according to this disclosure includes an insertion unit in a slim shape to be inserted into the rectum of a subject, the insertion unit comprising: an ultrasonic oscillator that transmits ultrasonic waves laterally to the insertion unit; and a shaft in a slim shape that is closer to the proximal side than the ultrasonic oscillator, and has an extension direction from the proximal side toward the distal side, the extension direction curving in the direction opposite to the direction in which the ultrasonic oscillator transmits the ultrasonic waves.

Advantageous Effects of Invention

According to a transrectal ultrasonic probe disclosed in this description, the transrectal ultrasonic probe can reduce the burden of a subject when inserted into the rectum of the subject. Alternatively, according to a transrectal ultrasonic probe disclosed in this description, the transrectal ultrasonic probe can be more easily inserted into the rectum of the subject.

BRIEF DESCRIPTION OF DRAWINGS

An embodiment of the present disclosure will be described based on the following figures, wherein.

DESCRIPTION OF EMBODIMENTS

Figure 1:
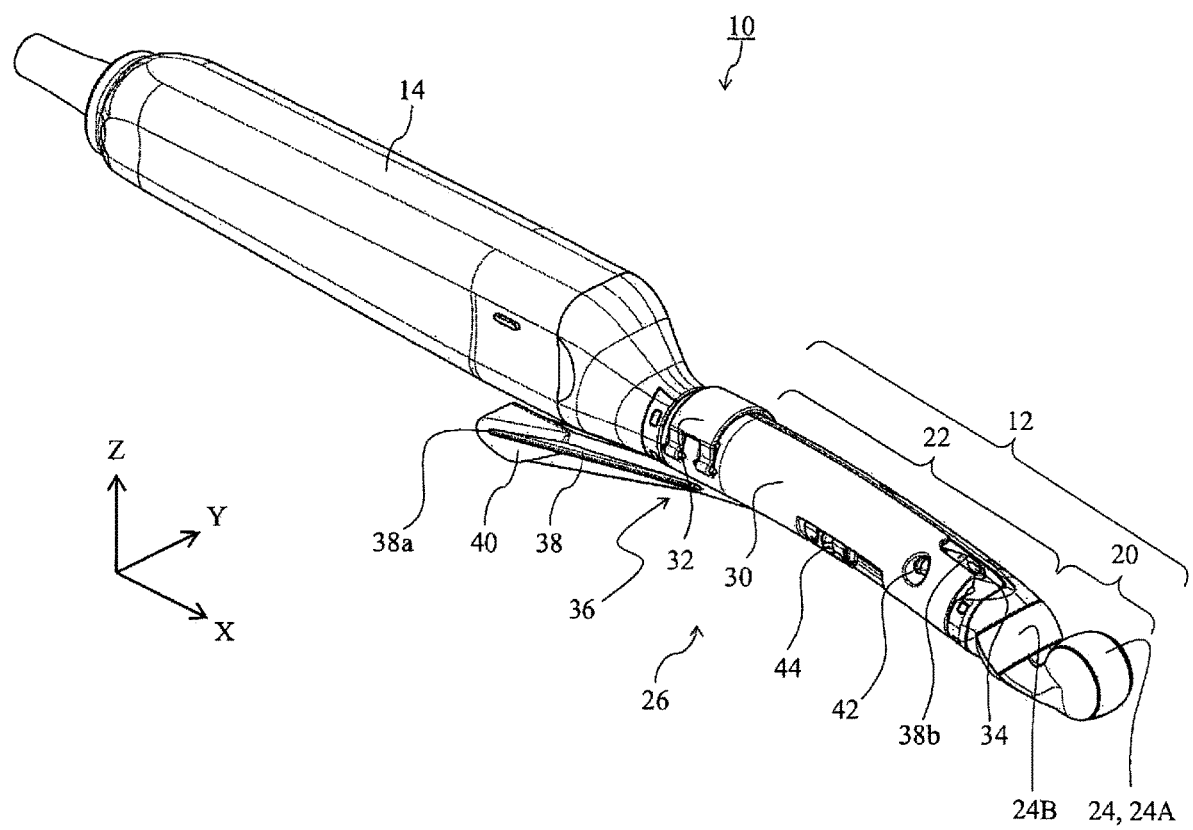
FIG. 1 is an external perspective view of a probe according to an embodiment.
Figure 2:
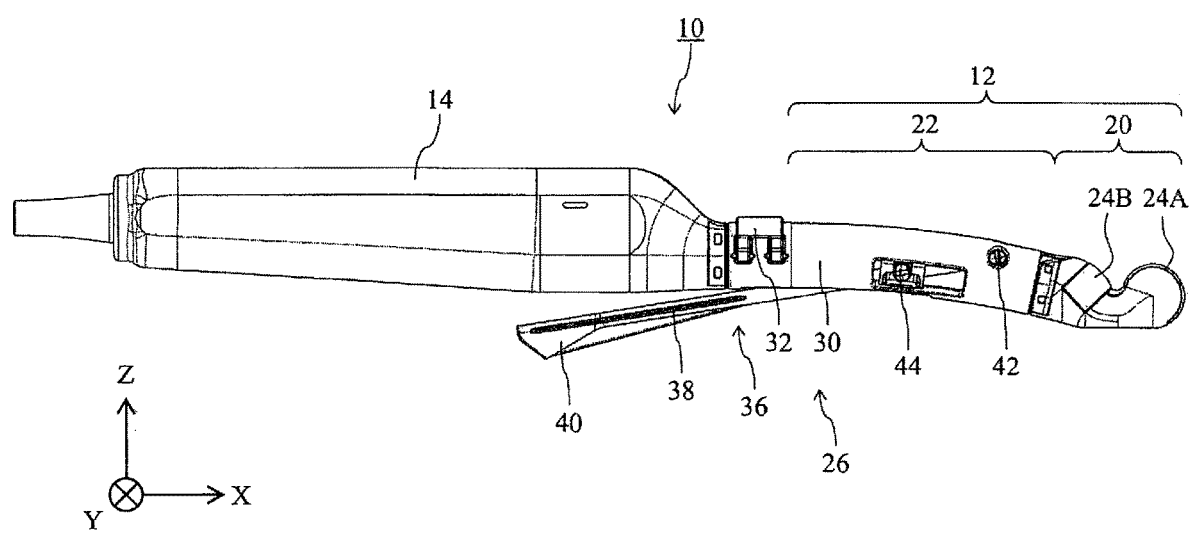
FIG. 2 is a side view of the probe according to the embodiment.

FIG. 1 is an external perspective view of a probe 10 according to this embodiment, and FIG. 2 is a side view of the probe 10. The probe 10 is a transrectal ultrasonic probe, a part of which is configured to be inserted into the rectum of a subject and transmit ultrasonic waves from the rectum to the test site and receive ultrasonic waves from the test site at the rectum. In particular, the test site is a prostate and the probe 10 can transmit ultrasonic waves from the rectum to the prostate and receive ultrasonic waves from the prostate at the rectum. The entire probe 10 has a slim shape. In FIGS. 1 and 2, the X axis represents the longitudinal direction of the probe 10 (the direction in which it extends (particularly, the direction in which the grip unit 14 described later extends)), the Y axis represents the lateral direction of the probe 10, and the Z axis represents the height direction. In this description, "front" refers to the positive side with respect to the direction of the X axis, "rear" refers to the negative side with respect to the direction of the X axis, "up" refers to the positive side with respect to the direction of the Z axis, and "down" refers to the negative side with respect to the direction of the Z axis.

The probe 10 is connected to an apparatus body (not shown in the drawing) through a probe cable (not shown in the drawing). Note that the probe 10 may be wirelessly connected to the apparatus body so that it can communicate with the apparatus body. The probe 10 transmits ultrasonic waves to the subject according to signals from the apparatus body, and transmits to the apparatus body electric signals responsive to the reflected waves from the subject. The apparatus body forms ultrasonic images based on the electric signals from the ultrasonic probe and displays the formed ultrasonic images on a display provided to the apparatus body.

The probe 10 includes an insertion unit 12 inserted into the rectum of the subject, and a grip unit 14 gripped by an operator such as a doctor. In this description, the insertion unit 12 side of the probe 10 is referred to as the "distal" side, and the grip unit 14 side is referred to as the "proximal" side. The insertion unit 12 has a slim shape and extends generally in the direction of the X axis (front-rear direction). The grip unit 14 also has a slim shape and extends in the direction of the X axis (front-rear direction). The insertion unit 12 is made thin for ease of insertion into the rectum, and the grip unit 14 is made thicker than the insertion unit 12 for ease of gripping by the operator. A probe cable extends from the proximal end of the grip unit 14 toward the apparatus body.

The insertion unit 12 has an insertion tip portion 20 at the tip, and a shaft 22 that is closer to the proximal side than the insertion tip portion 20 and connects the insertion tip portion 20 and the grip unit 14 together. In other words, the insertion tip portion 20 is connected to the distal end of the shaft 22.

The insertion tip portion 20 has a slim shape that extends in one direction. The insertion tip portion 20 has an acoustic head 24. The acoustic head 24 has an ultrasonic oscillator that transmits ultrasonic waves to the test site. In this embodiment, the acoustic head 24 has an oscillator array of aligned ultrasonic oscillators. The oscillator array converts, according to a signal from the apparatus body, the signal into ultrasonic waves, transmits the signal to the outside of the acoustic head 24; that is, the test site, receives the reflected waves from the test site, and converts the reflected waves to an electrical signal.

In this embodiment, the insertion tip portion 20 has two acoustic heads 24A and 24B. To be specific, the two acoustic heads 24A and 24B are aligned in the direction of the X axis, the acoustic head 24A is provided on the distal side, and the acoustic head 24B is provided on the proximal side. As will be described later in detail, the directions in which the ultrasonic waves are transmitted from the acoustic heads 24A and 24B, respectively, are parallel to each other, but the plane of ultrasonic radiation from the acoustic head 24A and the plane of ultrasonic radiation from the acoustic head 24B are orthogonal to each other. To be specific, the ultrasonic radiation plane from the acoustic head 24A is parallel to the XZ plane, and the ultrasonic radiation plane from the acoustic head 24B is orthogonal to the XZ plane. Since the probe 10 has two acoustic heads 24A and 24B, ultrasonic images of two surfaces related to the test site (prostate in this embodiment) can be captured. This allows the operator to easily grasp the test site in three dimensions.

The shaft 22 has a slim and generally tubular shape. As will be described later in detail, the shaft 22 is curved to reduce the burden on the subject during insertion into the rectum of the subject. The details of the curved shape of the shaft 22 will be described later.

The shaft 22 has a notch that is largely notched in the X axis. A puncture attachment 26 is attached to (fitted in) the notch. The puncture attachment 26 is a disposable member (single-use member) and is specifically detachably attached to the shaft 22.

The puncture attachment 26 includes a cover 30. In the state where the puncture attachment 26 is attached to the shaft 22 (hereinafter referred to as "attached state"), the shaft 22 and the puncture attachment 26 form a generally cylindrical shape together. To be specific, the cover 30 has a curved shape and, in the attached state, the outer surface of the shaft 22 and the outer surface of the cover 30 are substantially flush with each other, so that the overall cover 30 has a generally cylindrical shape. In particular, in the attached state, no protrusion is formed sideward from the shaft 22. This facilitates insertion of the shaft 22 into the rectum of the subject and suppresses the invasion of the subject.

As described below, the puncture attachment 26 includes a plurality of members that are generally situated within the cover 30 in the attached state. In the attached state, the attached state is maintained by an attachment lock 32 provided on the proximal side from the shaft 22.

The puncture attachment 26 includes a needle 34 and a needle guide member 36. The needle 34 is inserted into the test site by operator's operation for the purpose of collecting tissue of the test site, injecting a drug into the test site, or treating the test site. The needle 34 is made of a metal such as stainless steel.

The needle guide member 36 generally has a slim shape and is provided so as to extend in the X axis direction with a slight inclination so that its proximal end is lower than its distal end. The distal end of the needle guide member 36 is fixed within the cover 30 of the shaft 22, and the distal portion of the needle guide member 36 is situated within the cover 30. A notch for passing the needle guide member 36 is provided in a lower portion of the cover 30, and the proximal portion of the needle guide member 36 extends out downward from around the proximal end of the shaft 22 toward the distal side. The proximal end of the needle guide member 36 reaches the lower part of the grip unit 14. The proximal portion of the needle guide member 36 is not inserted into the rectum of the subject.

The needle guide member 36 has a straight tubular shape and includes an insertion member 38 through which the needle 34 is inserted, and a resin member 40 that supports the insertion member 38. The insertion member 38 and the resin member 40 are bonded to each other. The insertion member 38 defines the puncture route of the needle 34, and is made of a highly rigid member, for example, a metal such as stainless steel. The needle 34 is inserted into the insertion member 38 from the proximal end 38a of the insertion member 38, and goes out toward the distal side from the distal end 38b of the insertion member 38. Since the insertion member 38 has a straight tubular shape and is a highly rigid member, bending of the needle 34 passing therethrough is suppressed. The resin member 40 is a member having lower rigidity than the insertion member 38 and composed of, for example, a resin such as plastic. As will be described later, the needle guide member 36 is operated by the operator, and the resin member 40 is a portion gripped by the operator during operation.

In this embodiment, the distal end of the needle guide member 36 is locked with a guide shaft 42 extending in the lateral direction of the shaft 22 (that is, the direction of the Y axis). As a result, the needle guide member 36 is attached to the shaft 22 rotatably about the guide shaft 42 in the XZ plane. As described above, in the needle guide member 36, since the insertion member 38 and the resin member 40 are bonded to each other, rotation of the needle guide member 36 causes the insertion member 38 and the resin member 40 to rotate together about the guide shaft 42. Rotation of the insertion member 38 changes the inclination of the insertion member 38 in the XZ plane. Accordingly, the insertion direction of the needle 34 is changed.

The needle guide member 36 is rotated by the operator. In other words, the operator can change the insertion direction of the needle 34 by rotating the needle guide member 36. In particular, according to this embodiment, the straight tubular insertion member 38 rotates with the rotation of the needle guide member 36. This means that the entire puncture route of the needle 34 is rotated, so that the operator can puncture the test site without bending the needle 34.

The puncture attachment 26 may have a locking mechanism that restricts the rotation of the needle guide member 36 and locks the insertion direction of the needle 34. In this embodiment, the locking mechanism can lock the needle guide member 36 in any of a plurality of predetermined locking positions (a plurality of inclinations of the needle guide member 36). In other words, the locking mechanism can restrict the rotation of the needle guide member 36 so that the insertion direction of the needle 34 becomes any one of the plurality of predetermined insertion directions.

In this embodiment, a guide holding member 44 that restricts the rotation of the needle guide member 36 is provided as a locking mechanism. Although various methods can be adopted for restricting the rotation of the needle guide member 36 using the guide holding member 44, in this embodiment, the guide holding member 44 laterally holds the resin member 40 of the needle guide member 36, thereby restricting the rotation of the needle guide member 36. The guide holding member 44 is movable along the direction in which the shaft 22 extends and can be locked in any of the plurality of predetermined positions. The needle guide member 36 can be locked in one of the plurality of predetermined locking positions when the guide holding member 44 holds the needle guide member 36 in the position.

Although the rotation of the needle guide member 36 can change the insertion direction of the needle 34 as described above in this embodiment, the insertion direction of the needle 34 is not necessarily changeable and it may be inserted in a predetermined insertion direction.

Figure 3:
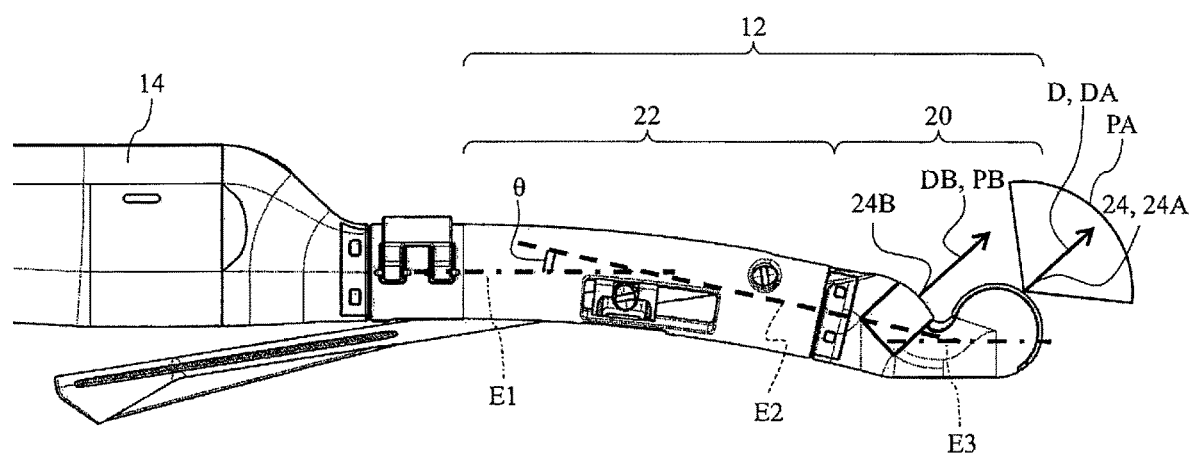
FIG. 3 is an enlarged side view of an insertion unit.

FIG. 3 is an enlarged side view of the insertion unit 12. The details of the shape of the insertion unit 12 will be described with reference to FIG. 3.

Before the details of the shape of the insertion unit 12, the direction of transmission of ultrasonic waves from the acoustic head 24 (oscillator array) will be described. In FIG. 3, the ultrasonic wave transmission direction DA from the acoustic head 24A and the ultrasonic wave transmission direction DB from the acoustic head 24B are indicated by respective arrows. As described above, in this embodiment, the transmission directions DA and DB are parallel to each other, the plane PA of ultrasonic radiation from the acoustic head 24A is parallel to the XZ plane, and the plane PB of ultrasonic radiation from the acoustic head 24B is orthogonal to the XZ plane.

In the following description, the acoustic head 24A and the acoustic head 24B are not distinguished, and these are simply referred to as the acoustic head 24. Similarly, the transmission direction DA and the transmission direction DB are not distinguished, and these are simply denoted as transmission directions D.

The oscillator array of the acoustic head 24 transmits ultrasonic waves laterally to the insertion unit 12. This means the transmission direction D is lateral to the insertion unit 12. The term "lateral" in this description refers to a direction different from the direction in which the insertion tip portion 20 extends. As will be described later, in this embodiment, the insertion tip portion 20 extends in the direction of the X axis (front-rear direction), and the "lateral" therefore refers to a direction different from the direction of the X axis (front-rear direction). In this embodiment, as shown in FIG. 3, the oscillator array of the acoustic head 24 transmits ultrasonic waves obliquely upward and forward from the surface of the acoustic head 24. In other words, the transmission direction D is obliquely upward and forward from the surface of the acoustic head 24.

As shown in FIG. 3, the shaft 22 has a gently curved shape. In particular, the shaft 22 is curved in the direction opposite to the direction D of ultrasonic wave transmission by the oscillator array of the acoustic head 24. To be specific, the shaft 22 is curved so that the extension direction from the proximal side to the distal side is curved in the direction opposite to the transmission direction D. As described above, in this embodiment, the transmission direction D is obliquely upward and forward, and the shaft 22 is therefore curved downward.

To be specific, the extension direction E1 in which the proximal end portion of the shaft 22 extends is parallel to the direction of the X axis (front-rear direction); that is, parallel to the direction in which the grip unit 14 extends. The ultrasonic wave transmission direction D is upward with respect to the extension direction E1, and the shaft 22 curves downward in the opposite direction. Hence, the extension direction E2 from the proximal side to the distal side of the distal end portion of the shaft 22 is downward, tilting with respect to the extension direction E1 in which the proximal end portion extends.

The angle θ between the extension direction E1 in which the proximal end portion of the shaft 22 extends and the extension direction E2 in which the distal end portion of the shaft 22 extends is set according to the anatomical shape of the rectum. To be specific, the angle θ is set to about five to eight degrees. In this embodiment, the angle θ is about six degrees.

In this embodiment, the shaft 22 is curved only downward (toward the negative side with respect to the Z axis) and is not curved in the direction of the Y axis.

The insertion tip portion 20 connected to the distal end of the shaft 22 extends in a direction curved with respect to the shaft 22 (a direction different from the direction in which the shaft 22 extends). In particular, the insertion tip portion 20 curves and extends in the direction D of ultrasonic wave transmission from the acoustic head 24 with respect to the shaft 22.

To be specific, as shown in FIG. 3, the extension direction E3 in which the insertion tip portion 20 extends curves toward the transmission direction D with respect to the extension direction E2 in which the distal end portion of the shaft 22 extends. Since the extension direction E2 is downward on the distal side, the extension direction E3 curves upward with respect to the extension direction E2. In other words, the inclination of the extension direction E2 is a negative value in the XZ plane, and "the extension direction E3 curves in the transmission direction D with respect to the extension direction E2" is rephrased as "the inclination of the extension direction E3 in the XZ plane is greater than that of the extension direction E2."

In this embodiment, the extension direction E3 of the insertion tip portion 20 is parallel to the direction of the X axis (front-rear direction); i.e., parallel to the extension direction E1 in which the proximal end portion of the shaft 22 extends and the direction in which the grip unit 14 extends.

Figure 4:
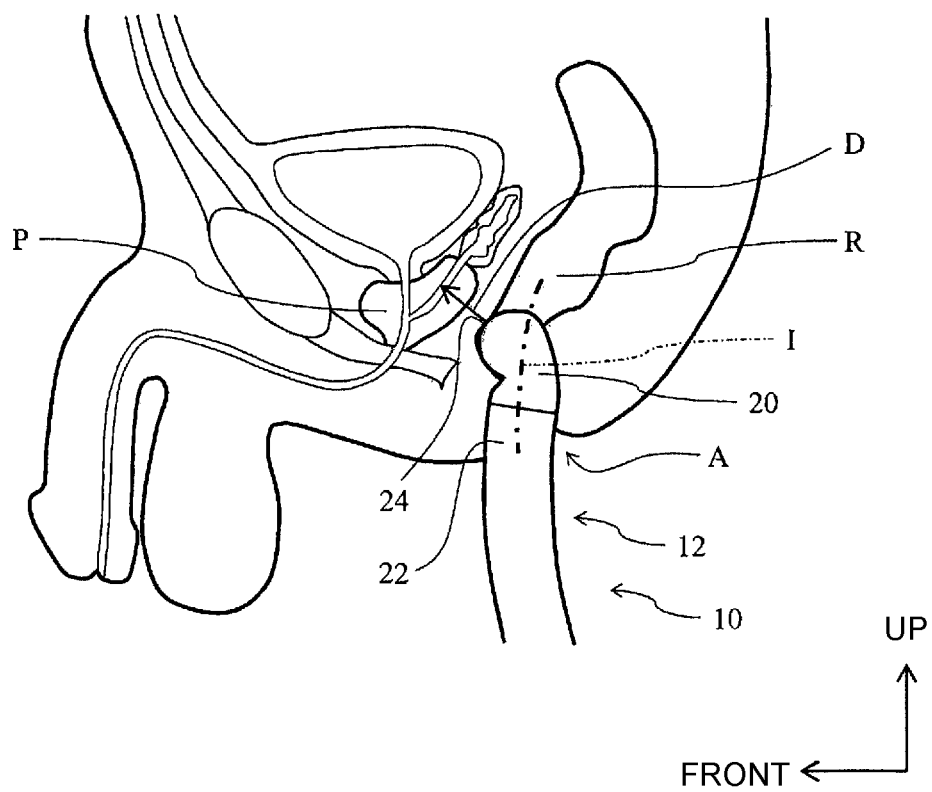
FIG. 4 is a sagittal section view of a rectum.

FIG. 4 is a sagittal section view showing how the insertion unit 12 of the probe 10 is inserted into the rectum R of the subject. As shown in FIG. 4, when viewed along the insertion route I of the insertion unit 12, the shape of the rectum R extending upward from the anus A is slightly curved rearward. Hence, while inserting the insertion unit 12 into the rectum R while the upper side of the probe 10 (the positive side with respect to the Z-axis direction of FIGS. 1 to 3) is directed toward the front side, the shaft 22 is curved to fit in the shape of the rectum R. This reduces the force of pressing the shaft 22 against the rectum R or the anus A, thereby reducing the burden on the subject when the insertion unit 12 is inserted into the rectum R. In addition, the operator can more easily insert the insertion unit 12 into the rectum R.

Further, in the state where the insertion unit 12 is inserted into the rectum R as shown in FIG. 4, the insertion tip portion 20 having the acoustic head 24 is curved forward with respect to the shaft 22. As a result, the direction D of ultrasonic wave transmission from the acoustic head 24 is just toward the prostate P. Therefore, an ultrasonic image of the prostate P can be suitably captured by transmitting and receiving ultrasonic waves through the acoustic head 24. Moreover, appropriately setting the insertion direction of the needle 34 enables a suitable puncture into the prostate P.

Although the embodiment of the transrectal ultrasonic probe according to this disclosure has been described above, the transrectal ultrasonic probe according to this disclosure is not limited to the aforementioned embodiment, and various modifications can be made without departing from the scope of this disclosure.

The invention claimed is:

1. A transrectal ultrasonic probe comprising an insertion unit in a slim shape configured to be inserted into a rectum of a subject, the insertion unit comprising:
   an ultrasonic oscillator that transmits ultrasonic waves laterally to the insertion unit; and
   a shaft in a slim shape that is closer to a proximal side of the transrectal ultrasonic probe than the ultrasonic oscillator, and having a first extension direction from the proximal side toward a distal side of the transrectal ultrasonic probe, the first extension direction curving in a direction opposite to a direction in which the ultrasonic oscillator transmits the ultrasonic waves,
   wherein the ultrasonic oscillator is provided in an insertion tip portion connected to a distal end of the shaft,
   wherein the insertion tip portion extends in a direction curving toward the direction in which the ultrasonic oscillator transmits the ultrasonic waves with respect to the shaft,
   wherein a second extension direction of the insertion tip portion is parallel to a third extension direction of a proximal end portion of the shaft, and
   wherein a length of a portion of the shaft that extends in the first extension direction is longer than a length of the proximal end portion of the shaft that extends in the third extension direction.

2. The transrectal ultrasonic probe according to claim 1, wherein an angle between the third extension direction of the proximal end portion of the shaft and the first extension direction of a distal end portion of the shaft is five to eight degrees.

3. The transrectal ultrasonic probe according to claim 1, further comprising:
   a needle configured to be inserted into a test site of the subject; and
   a needle guide member that includes a straight tubular insertion member through which the needle is to be inserted, and is contained in the shaft.

* * * * *